United States Patent
Sherman et al.

(10) Patent No.: US 9,119,907 B2
(45) Date of Patent: Sep. 1, 2015

(54) DIGITALLY CONTROLLED ASPIRATOR

(75) Inventors: Leslie H. Sherman, Denville, NJ (US);
George Beck, Mendham, NJ (US);
Richard Goetzl, Fort Lee, NJ (US);
Dorian LeCroy, New York, NY (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 774 days.

(21) Appl. No.: 11/231,498

(22) Filed: Sep. 21, 2005

(65) Prior Publication Data

US 2006/0122558 A1 Jun. 8, 2006

Related U.S. Application Data

(60) Provisional application No. 60/611,722, filed on Sep. 21, 2004.

(51) Int. Cl.
*A61M 1/00* (2006.01)

(52) U.S. Cl.
CPC ........... *A61M 1/0031* (2013.01); *A61M 1/0033* (2014.02); *A61M 2205/50* (2013.01)

(58) Field of Classification Search
CPC .......... A61M 1/0031; A61M 2205/50; A61M 1/0023; A61M 1/0033; A61M 2205/52; A61M 1/0035
USPC ................ 604/118–121, 22, 65–67; 128/276
See application file for complete search history.

(56) References Cited

U.S. PATENT DOCUMENTS

| | | | | |
|---|---|---|---|---|
| 3,812,855 A | * | 5/1974 | Banko | 604/31 |
| 3,920,014 A | * | 11/1975 | Banko | 604/31 |
| 4,024,866 A | * | 5/1977 | Wallach | 604/31 |
| 4,156,187 A | * | 5/1979 | Murry et al. | 324/142 |
| 4,180,074 A | * | 12/1979 | Murry et al. | 604/31 |
| 4,184,510 A | * | 1/1980 | Murry et al. | 137/565.23 |
| 4,289,158 A | * | 9/1981 | Nehring | 137/205 |
| 4,428,748 A | * | 1/1984 | Peyman et al. | 604/22 |
| 4,465,483 A | * | 8/1984 | Weilbacher | 604/317 |
| 4,493,698 A | * | 1/1985 | Wang et al. | 604/541 |
| 4,508,532 A | * | 4/1985 | Drews et al. | 604/22 |
| 4,529,401 A | * | 7/1985 | Leslie et al. | 604/131 |
| 4,622,503 A | * | 11/1986 | Sundblom et al. | 318/645 |
| 4,705,038 A | * | 11/1987 | Sjostrom et al. | 606/180 |
| 4,710,165 A | * | 12/1987 | McNeil et al. | 604/67 |
| 4,781,707 A | * | 11/1988 | Boehringer et al. | 604/317 |
| 4,857,063 A | * | 8/1989 | Glenn | 604/317 |
| 5,242,404 A | * | 9/1993 | Conley et al. | 604/119 |
| 5,733,256 A | * | 3/1998 | Costin | 604/22 |
| 5,807,358 A | * | 9/1998 | Herweck et al. | 604/320 |
| 6,171,072 B1 | * | 1/2001 | West et al. | 417/298 |
| 2005/0085772 A1 | * | 4/2005 | Zafirelis et al. | 604/131 |
| 2006/0122558 A1 | * | 6/2006 | Sherman et al. | 604/67 |

* cited by examiner

*Primary Examiner* — Bhisma Mehta
*Assistant Examiner* — Bradley Osinski
(74) *Attorney, Agent, or Firm* — The Webb Law Firm

(57) ABSTRACT

A digitally controlled aspirator is provided with a processor that allows the user to select operating conditions including one or more default settings. The processor further includes sensors for sensing operational and environmental conditions and adjusts the operation of the aspirator to reflect the sensed conditions.

11 Claims, 13 Drawing Sheets

| FIG.1A | FIG.1B | FIG.1C |
| --- | --- | --- |
| FIG.1D | | |

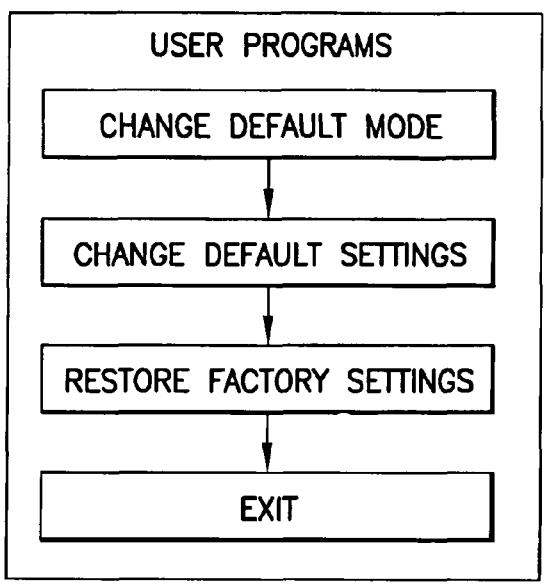
FIG.7
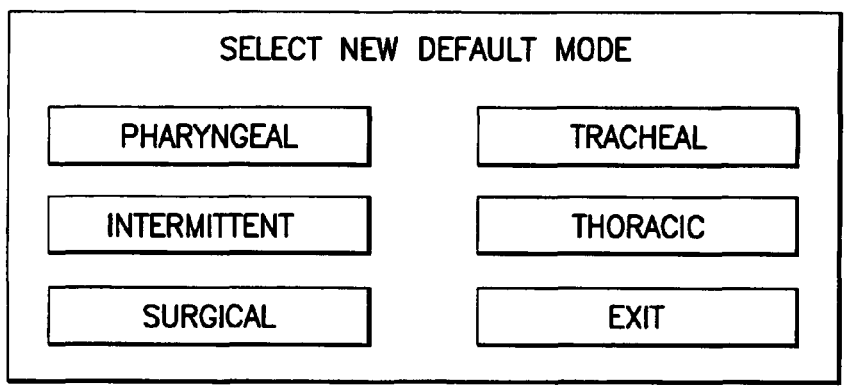
FIG.8
FIG.9
FIG.10

FIG.11

| FACTORY DEFAULT SETTINGS | | PHARYNGEAL | TRACHEAL | INTERMITTENT | THORACIC | SURGICAL |
|---|---|---|---|---|---|---|
| DEFAULT LIMIT SETTINGS | mmHg | 400 | 120 | 90 | | 400 |
| | cmH2O | | | | 25 | |
| | LPM | 35 | 35 | 8 | 20 | 50 |
| | ON SEC | | | 15 | | |
| | OFF SEC | | | 45 | | |
| RANGE | mmHg | 0–550 | 0–150 | 80–120 | | 0–550 |
| | cmH2O | | | | 20–220 | |
| | LPM | 20–40 | 20–40 | 6–10 | 15–35 | 20–70 |
| | ON SEC | | | 5–60 | | |
| | OFF SEC | | | 5–60 | | |

FIG.12

ACCEPT CURRENT SETTINGS?

VACUUM LIMIT: 400 mmHg
AIRFLOW LIMIT: 35 LPM

[YES] [NO]

FIG.13

CHANGE MODE SETTINGS

| CURRENT | | NEW |
|---|---|---|
| 400 | mmHg | [350] |
| | cmH2O | |
| 35 | LPM | [25] |
| | ON SEC | |
| | OFF SEC | |

[EXIT]

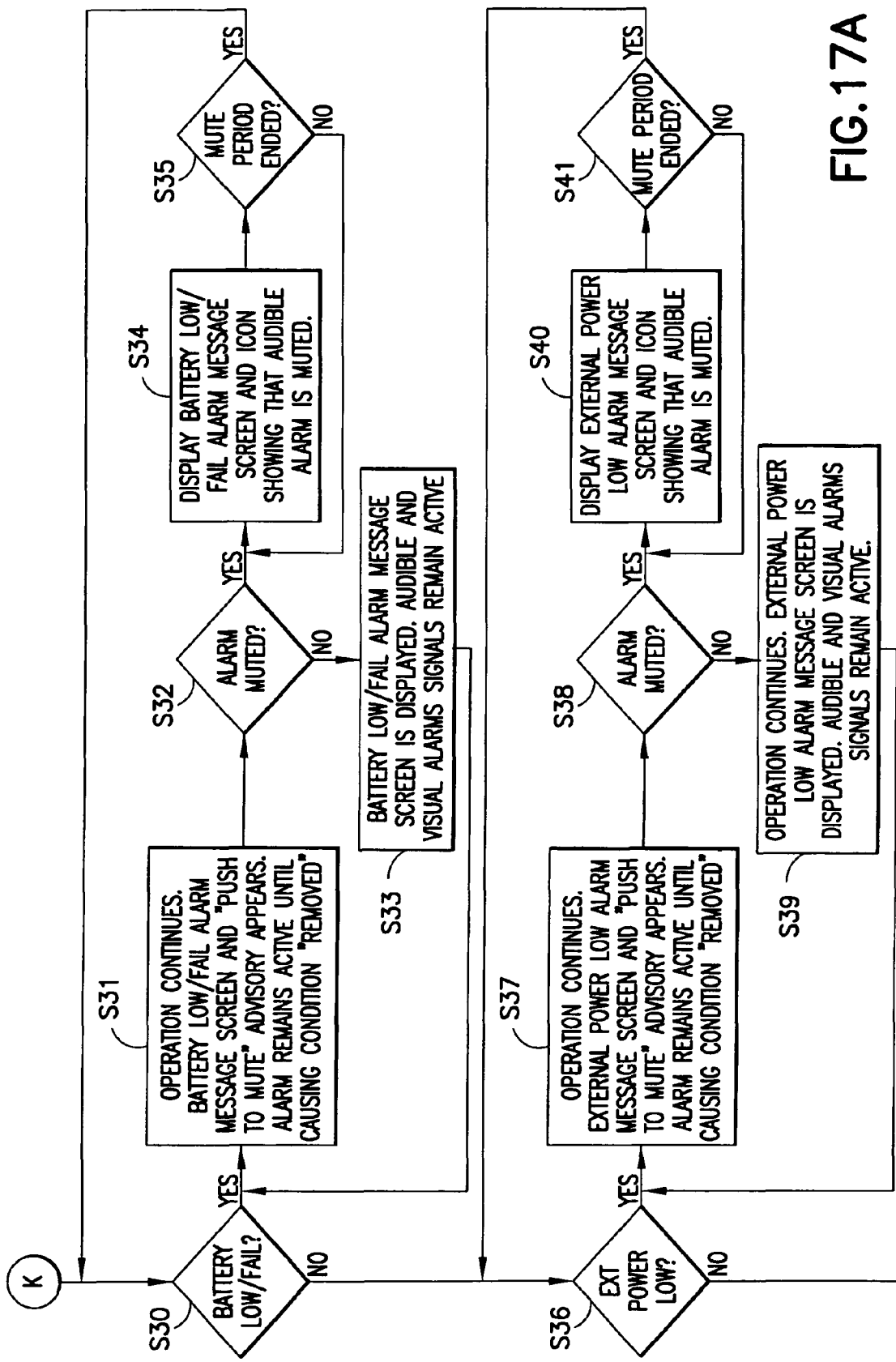

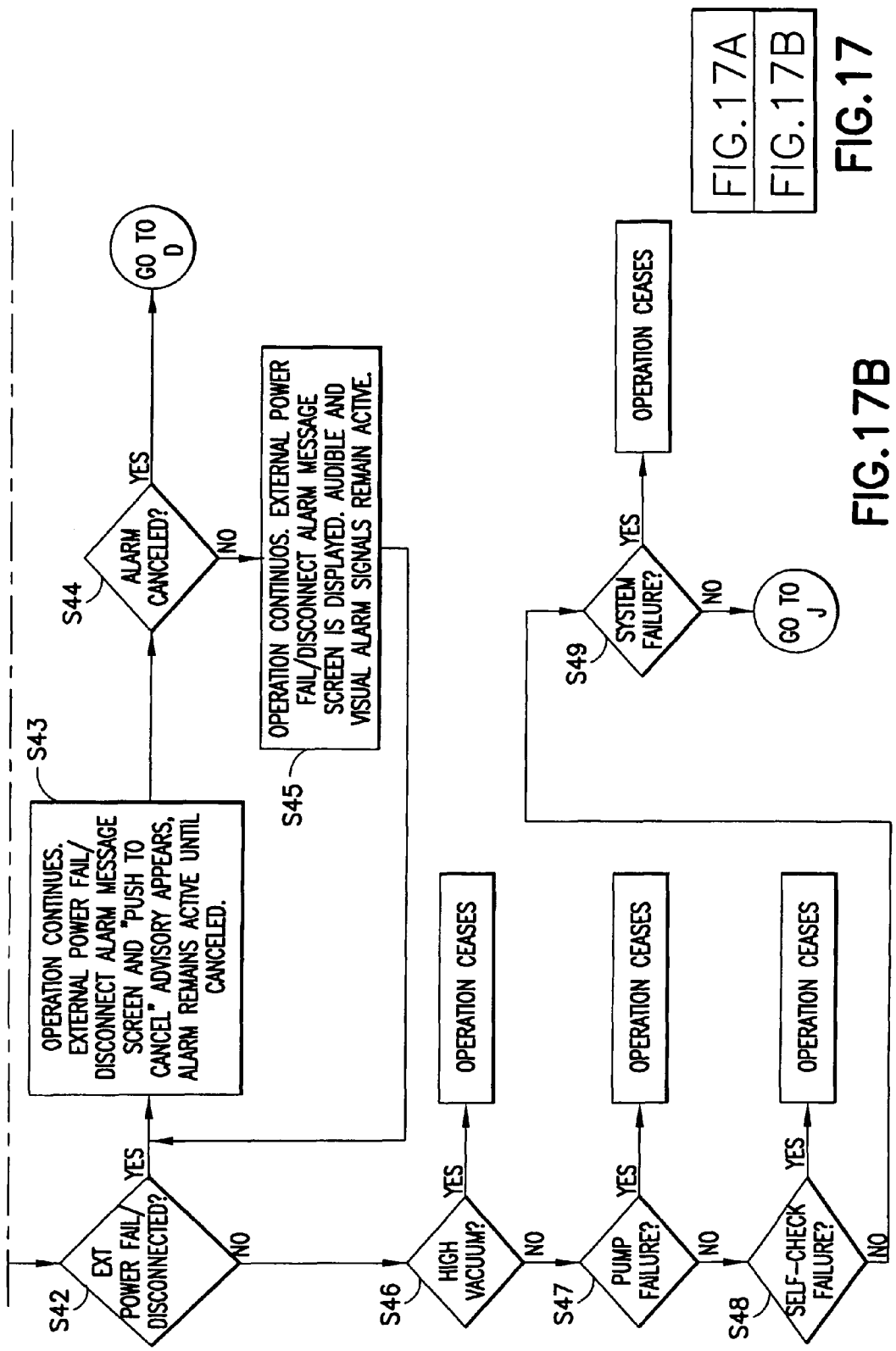

DIGITALLY CONTROLLED ASPIRATOR

This application claims priority on U.S. Provisional Patent Appl. No. 60/611,722, filed Sep. 21, 2004.

BACKGROUND OF THE INVENTION

1. Field of the Invention

The invention relates to a medical aspirator and, more particularly, to a system that is microprocessor-controlled and methods of control and operation therefor.

2. Description of the Related Art

Suction, or the application of a vacuum to a patient, has many uses within medicine. It is used within the pre-hospital care, home care and hospital environments to help clear a patient's airway, to remove debris from a surgical site, to provide gastrointestinal and wound drainage, and in some cases to help inflate a collapsed lung by providing mild negative pressure in the pleural cavity. Because of diversity within the patient population range (infant through adult) and the variety of procedures that are possible, each procedure has its own permissible vacuum and airflow ranges, and as a result, almost all suction devices are designed for a specific procedural use.

The usage environment has always dictated the types of suction apparatus that are commonly used.

In the pre-hospital care environments the primary use of portable devices is to provide relatively high vacuum and high airflow to the unprotected upper airway and to provide low vacuum and high airflow to the protected airway. The home care environment requires electrically powered devices that have adjustable vacuum (low to high) and high airflow for the removal of airway secretions as part of a patient's pulmonary toilet.

In the hospital environment a wide range of electrically powered suction devices is found. There are units whose performance is designed to provide suction and flow to the upper airway as described above; units that can provide high vacuum and high airflow to remove blood, bone and tissue debris from surgical sites; units that provide a mild vacuum and flow for drainage around wound sites; units that intermittently provide mild vacuum and flow for drainage of the gastrointestinal tract; units for draining the digestive tract; and units that provide low vacuum and high flow levels for pleural cavity evacuation. The required number of each type of suction apparatus is affected by seasonal patient population changes and the patient composition existing within these populations. This seasonal variability is quite common and results in many hospitals having to rent additional devices to augment their inventory.

Previous devices were limited in their ability to perform in more than two of the modes described above because their simple pneumatic controls lacked the ability to meet the flow, pressure and timing requirements inherent in the various operating modes. If an economically viable aspirator were available that met the gamut of clinical requirements, then civilians and military providers would have a single unit that meets their clinical and mission needs. In addition, a need has always existed for a multi-function suction apparatus for military or other remote pre-hospital or hospital applications.

Suction may be generated by pneumatic, manual power or electrical power.

Suction derived from manual power is generated when an operator physically causes a mechanical pump mechanism to be cycled back and forth. Manually powered suction devices produce irregular and difficult to control suction and are used almost exclusively in the emergency environment. Not surprisingly, their use is restricted to emergency suctioning of a patient's upper airway.

Suction derived from pneumatic power is generated when gas, flowing at high velocity past an orifice (venturi), produces a vacuum at the orifice. This occurrence is commonly referred to as the Bernoulli Effect. The amount of vacuum is controlled by increasing or decreasing the flow of gas past this orifice which may negatively impact the desired suction applied to the patient. This method typically uses oxygen as its source of gas power and is rarely used in the emergency and hospital environments anymore due to the large amounts of oxygen they consume. Pneumatically powered suction, when used, is limited mostly to emergency suctioning of a patients upper airway.

Suction derived from electrically powered sources may obtain its operating power from alternating current (AC), or direct current (DC), or from a battery pack or fuel cell. Electrically powered suction devices use a motor driven vacuum pump or thermally-cycled mechanisms to create suction. The characteristics of the pumps will ultimately determine the medical application to which they are applied. Electrically powered suction devices are the most common and are in widespread use throughout the pre-hospital, home care and hospital environments.

Designers have improved medical suction systems by incorporating smaller and/or more powerful pumps, state-of-the-art battery technology for portable variants and battery recharging technology related thereto, and via the use of more sophisticated collection reservoirs (both disposable and reusable) that incorporate mechanical shut-off valves and filters (both bacteriostatic and/or hydrophobic). Control of suction devices has been relegated to simple on/off switches and circuits, and vacuum limiting mechanisms that consist of bleed-type valves that entrain ambient air as a means by which to limit the vacuum applied to the patient. The interface to these devices consists of simple indicators such as illuminating lamps and/or mechanical vacuum gauges—typically of the bourdon-tube type.

In a few instances, designers have produced devices, capable of providing more than one mode of operation. The resultant devices are invariably bigger, heavier, more complex, more prone to malfunction and predicatively more expensive.

A very effective aspirator intended for use in ambulances is shown in U.S. Pat. No. 5,954,704. U.S. Pat. No. 5,954,704 is assigned to the assignee of the subject invention and the disclosure is incorporated herein by reference.

SUMMARY OF THE INVENTION

The invention relates to an aspirator with a vacuum pump/motor assembly that has a performance range sufficient to encompass the complete vacuum and airflow spectrum for all anticipated clinical uses, including those described above. Thus, the vacuum pump/motor assembly can be used to provide suction and flow to help clear a patient's airway, to remove debris from a surgical site, to provide gastrointestinal and wound drainage and to help inflate a collapsed lung by providing mild negative pressure in the pleural cavity.

The aspirator also may include a variable orifice valve that the processor uses to communicate with the vacuum pump for controlling vacuum levels. The processor preferably includes or communicates with one or more sensors for sensing vacuum pressure levels near the valve.

The aspirator also may include a motor speed control component and a tachometer that the processor uses for controlling airflow. The processor that instructs the motor speed control component to operate at a speed to generate an airflow based on an existing control setting for the set operating mode. The tachometer component communicates measured motor speed information back to the processor. Motor speed determines airflow rate. The processor then compares the information to determine whether the set flow rate equals the measured flow rate. If the flow set does not equal the flow measured, the processor will adjust the signal to the motor speed control component for causing the motor to speed up or slow down accordingly.

The aspirator further includes controls that enable an operator to vary the performance of the aspirator in accordance with a particular medical use. The controls enable the operator to set the duration of the vacuum from a continuous vacuum to an intermittent schedule in accordance with the needs of the particular medical procedure. The controls also enable the operator to select vacuum pressure levels and flow rates.

The actual vacuum pressure level at the site of aspiration is dependent on factors other than the particular operational rate of the vacuum pump. For example, the load at the site of aspiration can vary in accordance with conditions of a patient at any point in time. Power levels applied to the vacuum pump may be affected by local conditions, particularly when the aspirator is used at an emergency or non-hospital setting and when using a diminishing power source, such as a battery. The vacuum level also is dependent upon the altitude at which the aspiration is being carried out. In this regard, an aspirator often is used in a medical evacuation helicopter or in geographical locations substantially higher than sea level. Accordingly, the aspirator apparatus of the subject preferably includes a closed loop feedback control. Thus, the operator may employ the control of the microprocessor to set a desired vacuum pressure level and airflow rate. The operator then may command the device to maintain this level and rate under various conditions. In a preferred embodiment, the apparatus automatically compensates for altitude variations by adjusting the operation of the vacuum pump in accordance with sensed changes in barometric pressure so that a preset vacuum pressure level can be maintained automatically.

The control of the aspirator preferably is achieved by a microprocessor that communicates with the vacuum pump, the sensors and the controls. The microprocessor is operative to respond to signals from the controls and the sensors and to modify the vacuum output of the vacuum pump to meet a particular medical use.

The aspirator of the subject invention further includes output means for outputting relevant information to the operator. The output means provides the operator with required operating information and may generate alarm signals under certain operating conditions. The output display preferably is operative to compensate for real time changes in ambient atmospheric conditions, such as those changes that are attributable to altitude changes in a non-pressurized or partly pressurized environment.

The microprocessor of the aspirator preferably is preprogrammed with default settings for vacuum and airflow set points. The default settings preferably conform to current clinical standards. Thus, the aspirator can be used immediately upon receipt by the operator without prior calibration. However, the controls of the aspirator preferably enable the operator to reconfigure a default setting based on the preference of the operator or based on local operating conditions.

The microprocessor may include an applications programming interface so that the operator may configure the microprocessor. Additionally, the applications programming interface enables the operator to request certain operational data and receive current status information based on the requests. The interface may further be configured to permit remote operation and control. Additionally, the interface may permit a plurality of aspirators to be controlled by a single controller. As a result, a single controller can provide input to several aspirators and can receive current status information from a plurality of aspirators.

The operator controls preferably are simplified for ease of operation. In this regard, the controls may comprise a power switch. A rotary encoder may be provided as part of or separate from the power switch. The rotary encoder enables an operator to select an operational mode or operational settings from several optional parameters permitted by the logic of the processor.

The controller may be operative to provide menu driven operating protocols. Thus, the user may select the appropriate mode of operation through a plurality of sequential command options. One selection of a mode of operation may be followed by prompts that guide the user to select safety defaults for protecting a patient from exposure to an inappropriate level of vacuum pressure or airflow.

BRIEF DESCRIPTION OF THE DRAWINGS

FIG. 7 is a schematic illustration of a fourth preferred display provided by the LCD display of the apparatus.

FIG. 8 is a schematic illustration of a fifth preferred display provided by the LCD display of the apparatus.

FIG. 9 is a schematic illustration of a sixth preferred display provided by the LCD display of the apparatus.

FIG. 10 is a schematic illustration of a seventh preferred display provided by the LCD display of the apparatus.

FIG. 11 is a schematic illustration of a eighth preferred display provided by the LCD display of the apparatus.

FIG. 12 is a schematic illustration of a ninth preferred display provided by the LCD display of the apparatus.

FIG. 13 is a schematic illustration of a tenth preferred display provided by the LCD display of the apparatus.

FIG. 17 is a flow chart illustrating preferred operations pertaining to the triggering of the alarm.

DETAILED DESCRIPTION OF THE PREFERRED EMBODIMENTS

Figure 1A:
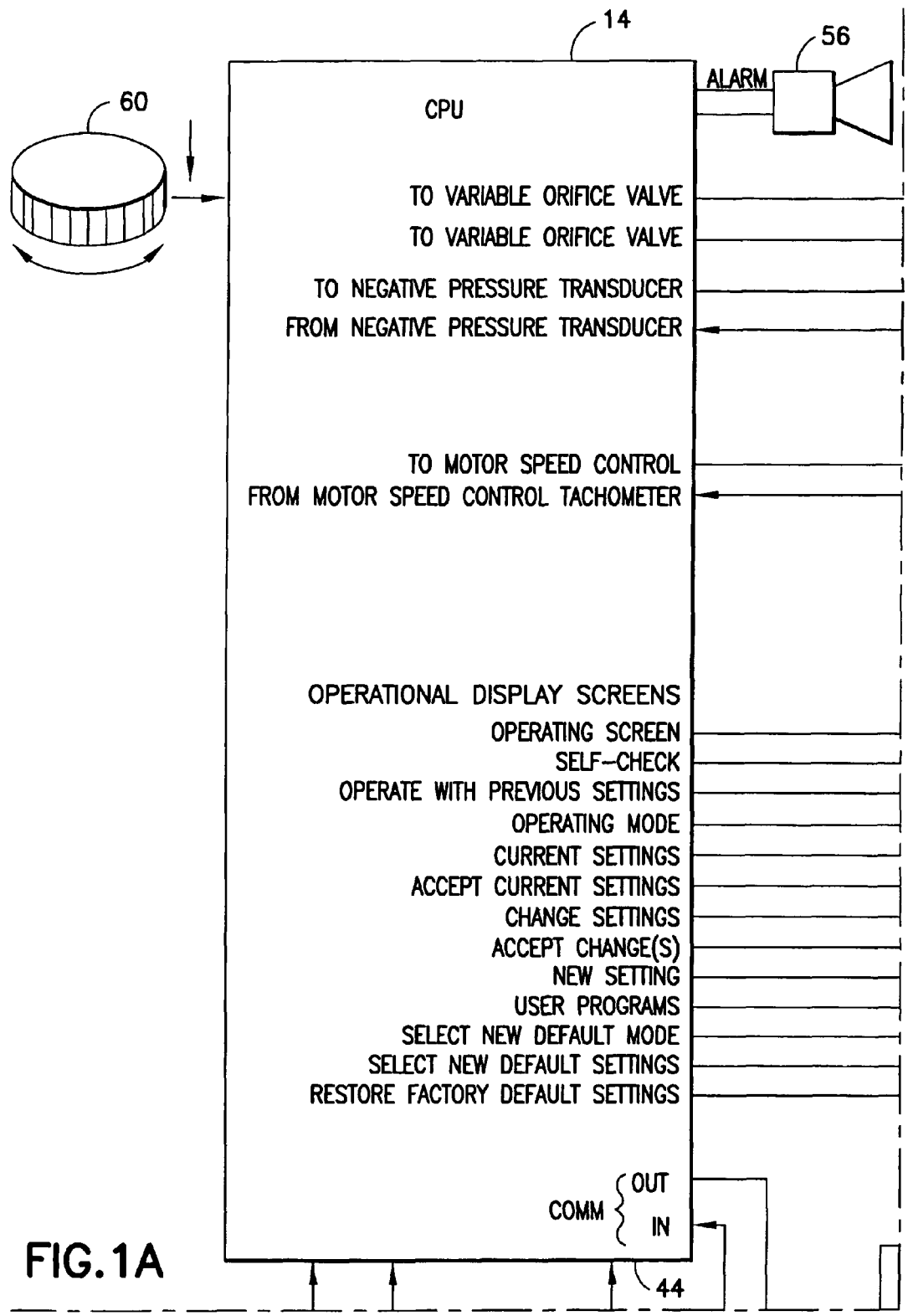
FIG. 1 is a schematic view of an aspirator in accordance with one preferred embodiment of the subject invention.
Figure 1B:
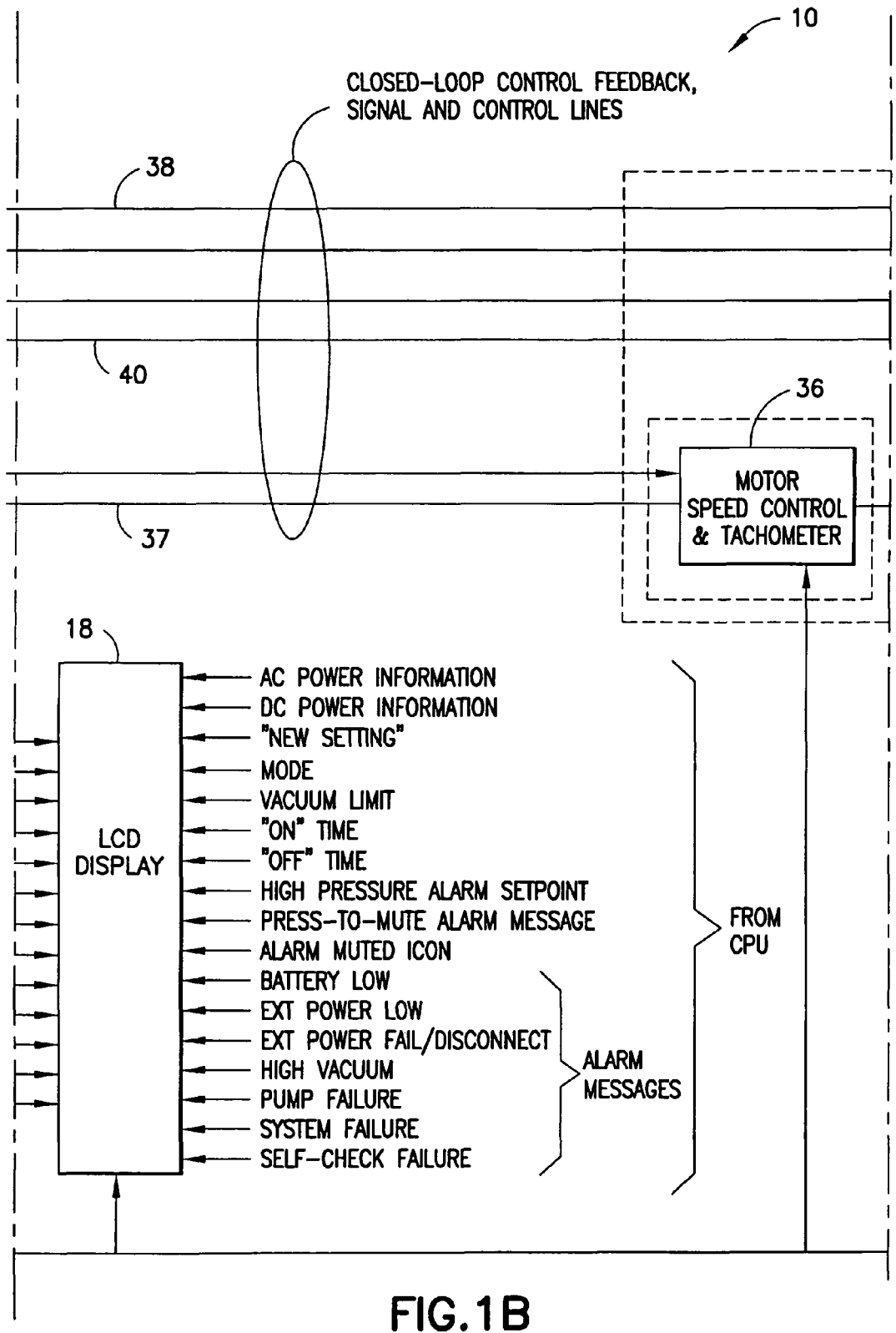
Figure 1C:
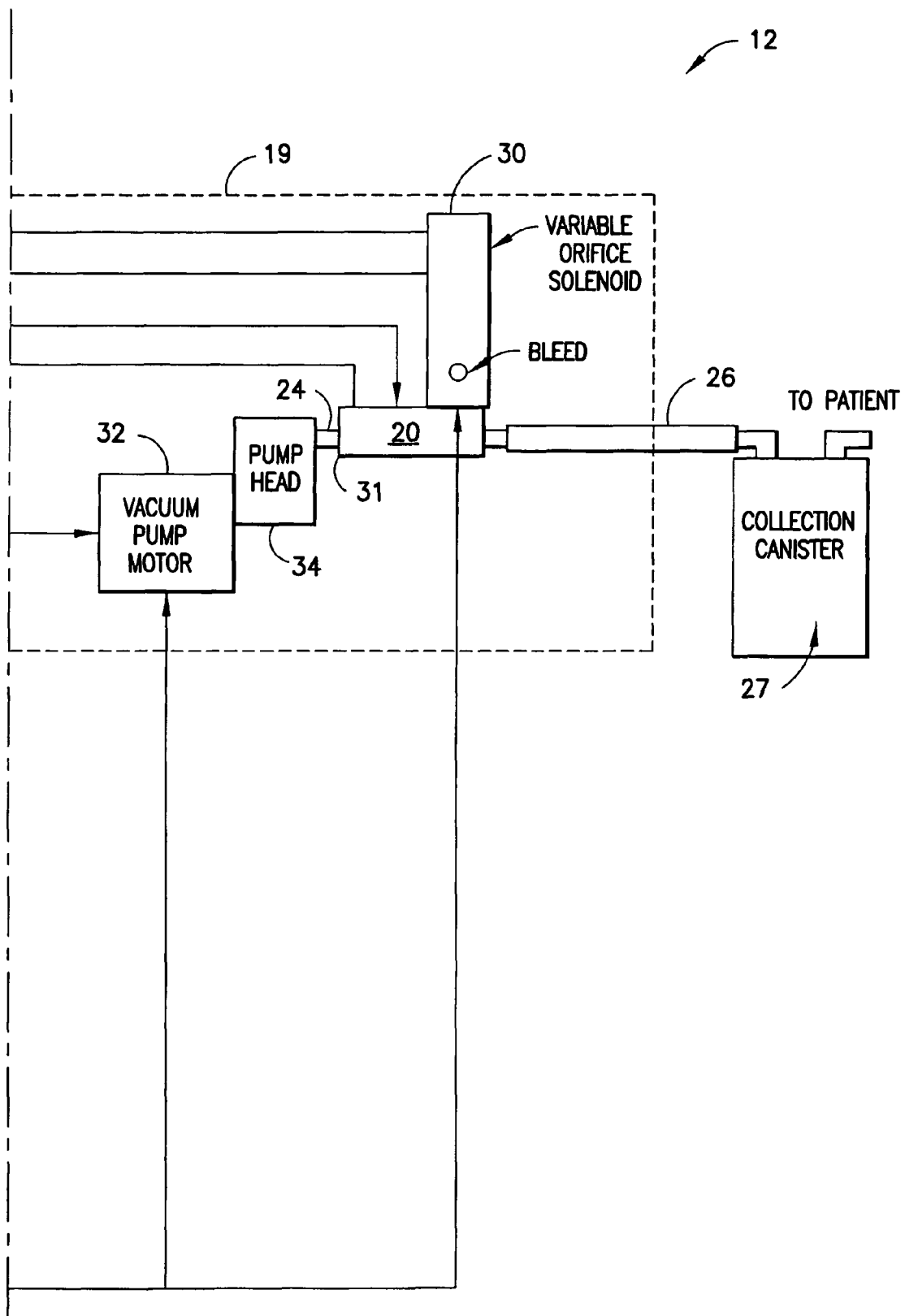
Figures 1, 1D:
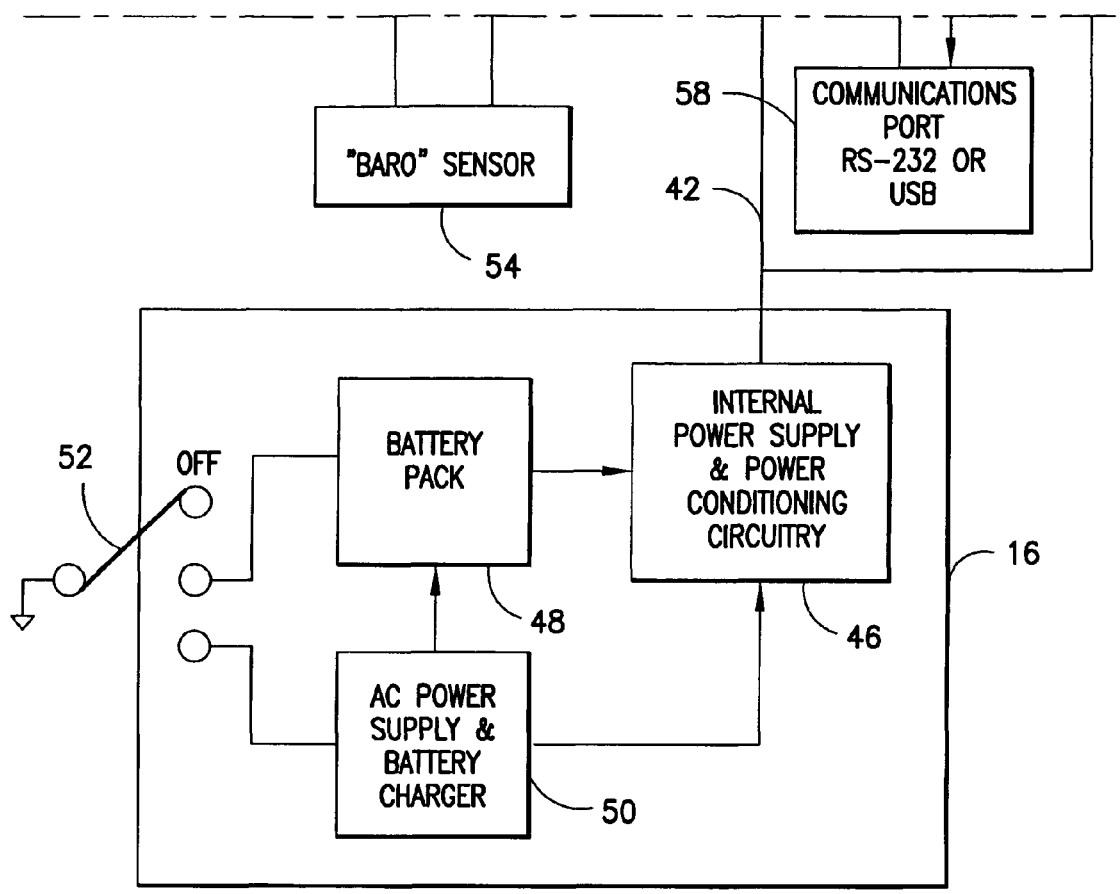

An aspirator in accordance with a preferred embodiment of the subject invention is identified generally by the numeral 10 in FIG. 1. The aspirator 10 includes a suction apparatus 12, a processor 14, a power supply 16 and a display 18. The apparatus 10 further include additional inputs and outputs as explained further below.

The suction apparatus 12 includes a manifold 20 with a fluid inlet 22 and a fluid outlet 24. A tube 26 is mounted to the fluid inlet 22 of the manifold 20 and communicates with a collection canister 27 disposed externally on the aspirator 10 and connected to the suction apparatus 12. The collection canister 27 in turn communicates with a hose and an appropriate suction catheter (not shown) that can be placed in communication with the patient. The exact configuration of the collection canister 27 and the suction catheter will vary in accordance with the specific medical use for the apparatus 10 and may be of prior art design. In this regard, a known collection canister is shown in the above-referenced U.S. Pat. No. 5,954,704.

The manifold 20 further includes a variable orifice electronic valve 30, such as a solenoid valve, that controls an air bleed between the fluid inlet 22 and the fluid outlet 24. The electronic valve 30 can adjust the amount of the air bleed over the range between a fully opened condition and a fully closed condition. Additionally, the variable orifice electronic valve 30 can be operative to open and close at a selected frequency or duty rate. Operation of the electronic valve 30 is controlled by the processor 14 as explained further herein. The manifold 20 further includes a transducer 31 for sensing the negative pressure level at the manifold 20 and for generating a signal indicative of the value of the sensed negative pressure. The transducer 31 communicates with the processor 14 as explained herein.

The suction apparatus 12 further includes a vacuum pump motor 32 that communicates with a pump head 34. The pump head 34 in turn communicates with the fluid outlet 24 of the manifold 20. The vacuum pump motor 32 and the pump head 34 cooperate to generate a negative pressure when the suction catheter becomes fully or partially occluded. The suction apparatus 12 further includes a motor speed control and tachometer 36 for controlling the operating speed of the vacuum pump motor 32 and for producing an output signal to indicate the actual speed of the vacuum pump motor 32. The motor speed control and tachometer 36 communicates with the processor 14. The motor speed control component receives information from the processor 14 that tells it to generate an airflow based on the current control setting for the set operating mode. The tachometer component communicated information back to the processor 14 and compares the information to see whether the flow set equals the flow measured. If the flow set does not equal the flow measured, the processor 14 will adjust the signal to the motor speed control component causing the motor to speed up or slow down accordingly.

As illustrated herein, the vacuum pump motor 32, the pump head 34 and the motor speed control and tachometer 36 are included in the housing 19 of the suction apparatus 12. However, one or all of these components can be disposed externally of the housing 19. For example, the vacuum pump motor 32 and the pump head 34 can be in the housing 19, while the motor speed control and tachometer 36 can be in a separate external module that may include the processor 14. Alternatively, the vacuum pump motor 32 and pump head 34 can be disposed externally of the housing 19 in a separate motor housing. The motor speed control and tachometer 36 can be in the same motor housing, in the suction apparatus 12 or in the processor 14.

The processor (CPU) 14 of the aspirator 10 is in two-way communication with the suction apparatus 12 to provide a closed-loop feedback between the suction apparatus 12 and the processor 14. In particular, processor 14 has connections 38 to and from the variable orifice valve 30 and connections 40 to and from the negative pressure transducer 28 in the manifold 20. The functional implications of the connections 38 and 40 as part of the closed-loop control feedback is described further below.

The power supply 16 includes a connection 42 to a power input port 44 of the processor 14 so that the power supply 16 provides sufficient power for operating the suction apparatus 12, the processor 14, the display 18, the motor speed controller and tachometer 36, the vacuum pump motor 32 and the variable orifice electronic valve 30. The power supply 16 includes an internal power supply and power conditioning circuit 46 connected to the power input port 44 via the connection 42. The power supply 16 further includes a battery pack 48 connected to the internal power supply and power conditioning circuit 46 for providing one optional power source. The power supply further includes an AC power supply and battery charger unit 50 connected to an external power supply and further connected to both the internal power supply and power conditioning circuit 46 and the battery pack 48. A switch 52 is mounted to the power supply 16 and is operative for selectively switching between an off mode, a battery power mode and an AC power mode. When the switch is turned to the AC power mode, the AC power supply and battery charger 50 supplies power to the battery pack 48 for recharging the battery pack and further supplies power to the internal power supply and power conditioning circuit 46 for powering the aspirator 10.

The display 18 preferably is an LCD display that is connected directly to the processor 14. The display 18 is operative for displaying a broad range of operating conditions as shown in FIG. 1 and as described further herein. Additionally, the LCD display may be a touch sensitive display that permits the operator to select sequential arrays of menu options as described below.

The processor 14 includes other inputs and outputs independent of the suction apparatus 12, the power supply 16 and the display 18. Significantly, the processor 14 is connected to a barometric sensor 54 that senses ambient barometric pressure conditions and provides barometric pressure data to the processor 14 on a real time basis. The processor 14 uses data from the barometric sensor 54 with data sensed by the pressure transducer 31 to vary the operation of the variable orifice valve 30 and the motor speed controller and tachometer 36.

The aspirator 10 further includes an alarm 56 connected to the processor 14 and operative to produce an audible and/or visible alarm in response to certain conditions input to the processor 14. For example, the processor 14 will trigger the alarm 56 in response to extreme ranges of vacuum, a pump failure, a power failure or the like as illustrated in FIG. 1.

The processor 14 further includes a communication port 58, such as a USB or RS-232. The communication port 58 enables connection to a remote controller which can monitor and control the aspirator 10 from a remote location. Hence, a plurality of aspirators 10 can be controlled from a single remote location, while each aspirator 10 provides real time data at the communication port 58.

Figure 2A:
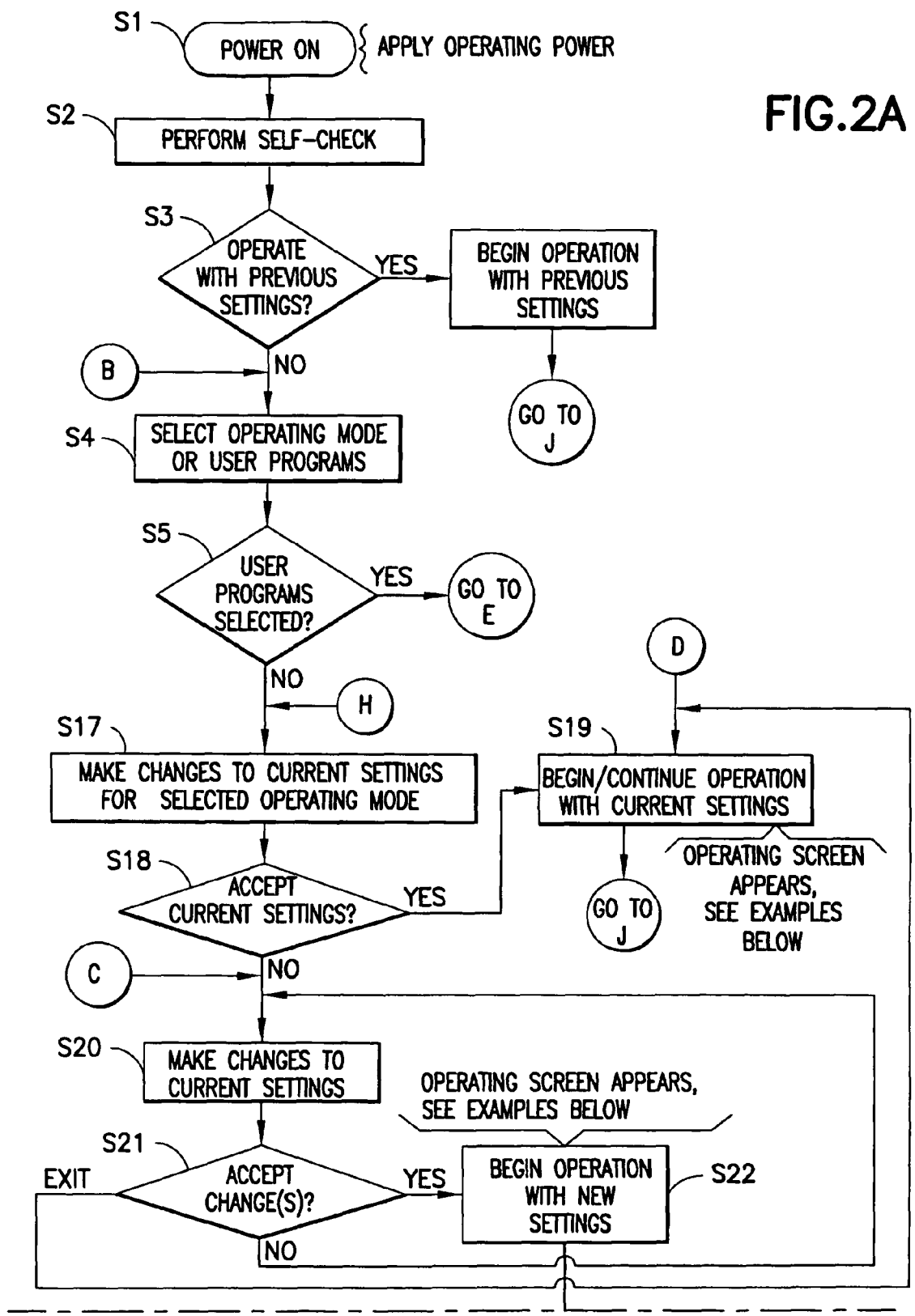
FIG. 2 is a flow chart illustrating one preferred operational method of the subject invention.
Figure 2B:
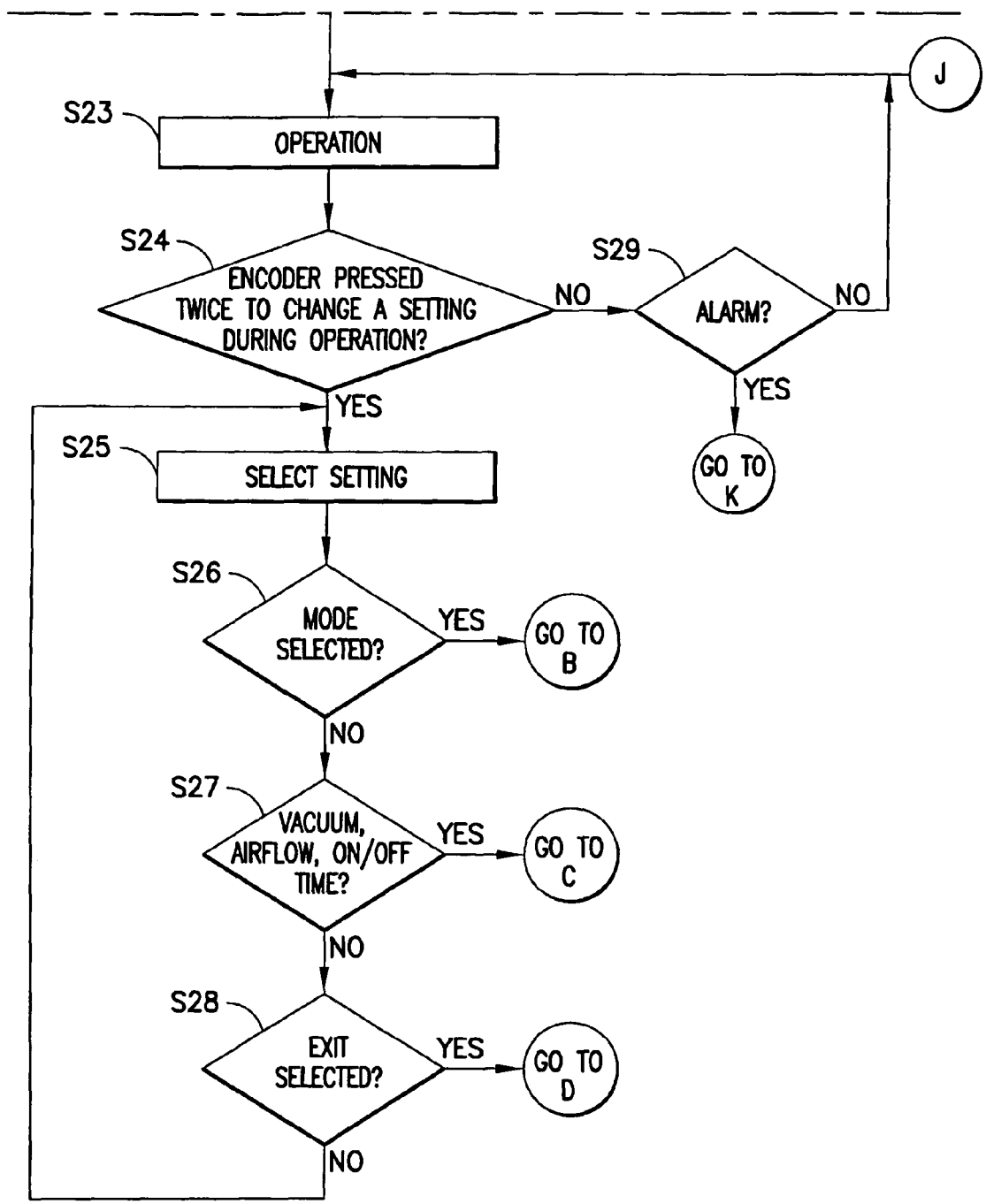
Figure 3:
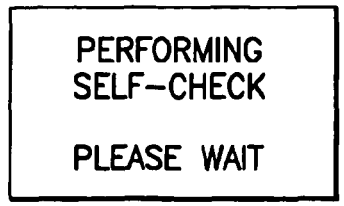
FIG. 3 is a schematic illustration of a first preferred display provided by the LCD display of the apparatus.
Figure 4:
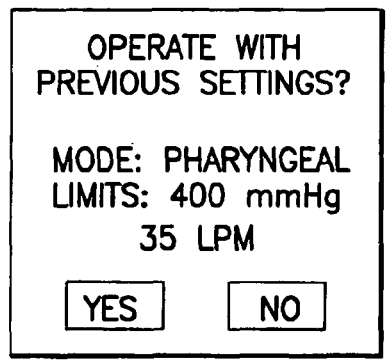
FIG. 4 is a schematic illustration of a second preferred display provided by the LCD display of the apparatus.

FIGS. 2-11 show one optional operating procedure for the aspirator 10. With reference to FIG. 2, a first step S1 of the procedure requires the operator to actuate the switch 52 of the power supply 16 in FIG. 1 for supplying power either from the battery pack 48 or the AC power supply 50. The processor 14 then will perform a self check for the various components of the aspirator 10 as indicated schematically by step S2 in FIG.

2. As part of this step, the processor 14 will cause the display 18 to display a screen image, such as the preferred image shown in FIG. 3.

Upon completion of the self check in step S2, the processor 14 will allow the operator to choose between operations with the previous settings or with new settings as indicated at step S3. As part of this step, the processor 14 will cause the display 18 to display a screen image, such as the preferred image illustrated schematically in FIG. 4. More particularly, the screen image will display the previous operational mode (e.g., pharyngeal) and operational limits (e.g., pressure level in mm of mercury and flow rate in liters per minute LPM). In many instances, the operator will choose to begin operations with the previous setting, and the screen of FIG. 4 will be programmed to indicate acceptance of the previous settings. As a result, the user need merely press the rotary encoder push button switch 60 shown in FIG. 1 to enter the "YES" selection. The process then will proceed to step S4 and to the operational start phase at input location J shown in FIG. 2. In other instances, the operator will want to select a new operating mode or program. As noted above, the processor 14 initially will cause the display 18 to display the acceptance of the previous settings. Thus, to change the setting, the operator will turn the rotary encoder push button switch 60 of FIG. 1. This will cause the "NO" image on the preferred display of FIG. 4 to be illuminated. The operator then will press the rotary encoder push button switch 60 so that the processor 14 will direct the operator through the steps of selecting a new mode and/or program.

Figure 5:
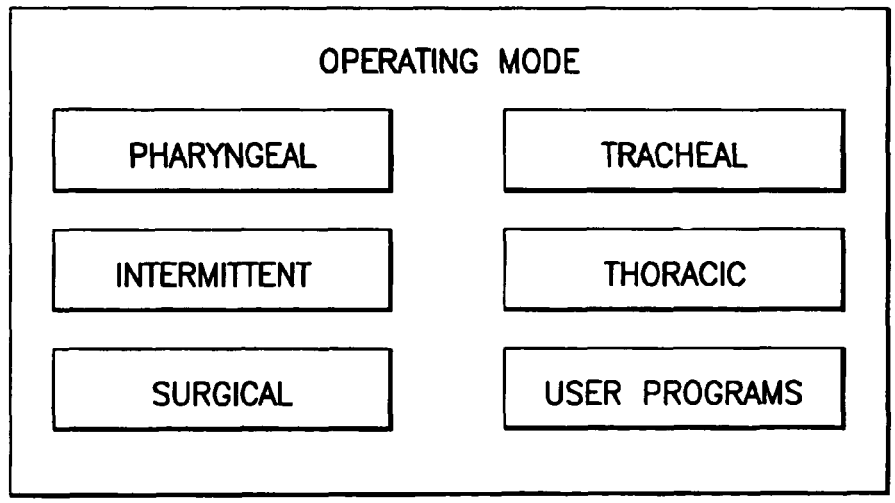
FIG. 5 is a schematic illustration of a third preferred display provided by the LCD display of the apparatus.
Figure 6:
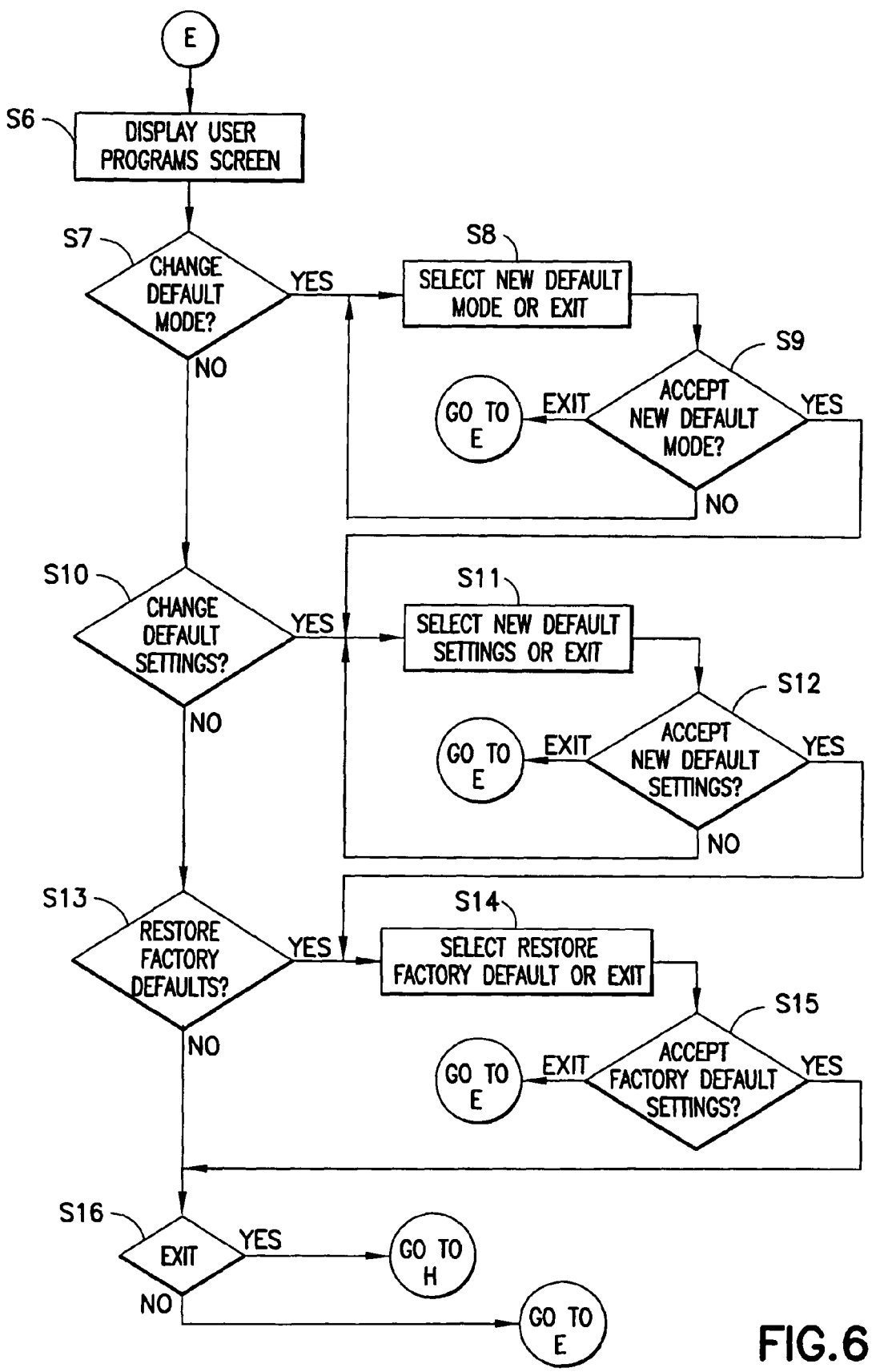
FIG. 6 is a flow chart illustrating a preferred procedure for changing operational modes, settings and defaults.

The processor 14 will lead the operator through a series of menu options for selecting the appropriate mode and/or user program as indicated at step S4. At this step, the processor 14 will cause the display 18 to display an image, such as the preferred image shown in FIG. 5. The operator then will turn the rotary encoder push button switch 60 until the appropriate operational mode is illuminated. The operator then will push to rotary encoder push button switch 60 when the preferred operational mode has been illuminated. One option provided by the screen of FIG. 5 is to select user programs distinct from the five optional operating modes of FIG. 5. Step S5 indicates the process step where the processor 14 determines whether the user programs option has been selected. In those instances where the user programs are selected, the processor will proceed to step S6 as illustrated in FIG. 6. In this step, the processor 14 will cause the display 18 to identify the optional user programs that can be changed or restored. A typical screen image is illustrated in FIG. 7 and displays to the user the option of changing default mode, changing default settings, restoring factory settings or exiting from the user programs option. The user will employ the rotary encoder switch 60 until the processor 14 causes the display 18 to illuminate the selected program option.

Step S7 identifies a step where the processor 14 determines whether the operator has selected a change in the default mode. If this change has been selected, the processor 14 will proceed to step S8 to permit the operator to select the new default mode or to "exit" if the operator determines that the existing default mode is acceptable. FIG. 8 shows an optional preferred screen display that will permit the operator to select a new default mode or to exit from this user program option. Once again, the operator will use the rotary encoder push button switch 60 to choose the appropriate option in FIG. 8 and then to confirm that selection.

The processor 14 will require the operator to confirm the selection made in step S8. This confirmation step is a fail safe procedure and is illustrated by step S9 in FIG. 6. If the user chooses in step S9 not to accept the new default mode, the processor 14 will return the operator to step S8 for selecting a new default mode or for exiting from this option. If the user chooses in step S9 to exit from this changing default mode option, the processor 14 will return the operator to step S6. If the user chooses in step S9 to accept the new default mode then the processor 14 will direct the user to steps for selecting default settings for the selected default mode as explained below.

The operator, in step S7, may choose not to change the default mode. Under these conditions, the processor will determine in step S10 whether the operator wants to change the default settings. The operator will indicate a desire to change the default setting by rotating the rotary encoder push button switch 60 until the change default setting has been identified, such as in the preferred screen image shown in FIG. 7. The operator then will press the rotary encoder push button switch 60. Under these conditions, the processor will proceed to step S11. FIG. 6 also shows that step S11 will be reached under those conditions where the operator has chosen to accept the new default mode in step S9. The processor 14 will cause the display 18 to display the optional default settings as illustrated in the preferred screen image of FIG. 9. The operator then will use the rotary encoder push button switch 60 for choosing each of the optional settings. One of the optional settings shown in FIG. 9 is "Exit" which will be selected if the operator has determined that a different user program option should have been selected. After making the selections offered by FIG. 9 and as part of step S11, the processor will require the operator to confirm the new default settings, as illustrated in step S12. One option is for the operator to exit this decision making step. In response to a selection of the exit option, the processor 14 will direct the user back to step S6 for selecting one of the optional programs. Alternatively, the operator could choose not to accept the default settings in step S12. Under this selection, the processor 14 will return the operator to step S11 and FIG. 9 so that the operator can choose new default settings or exits from this decision process. Of course, step S12 permits the operator to accept the new default settings. Under these circumstances, the processor 14 will proceed to a step for restoring factory defaults. The processor 14 will proceed to determine whether the operator has chosen to restore the factory defaults.

The operator may choose in step S10 not to change the default settings. As a result, the processor then will determine in step S13 whether the operator chooses to restore the factory default settings. This preferred decision making screen is illustrated in FIG. 10, and the operator is given the option of either exiting or restoring the factory default settings. An operator who chooses to restore factory defaults will be directed by the processor to step S14 and to the preferred screen image shown in FIG. 11. The processor then will direct the operator in step S15 to either accept the factory default setting or to exit from this decision making process. An operator who chooses to exit from step S15 will be directed back to step S6 and to the preferred screen of FIG. 7. A user who chooses to accept the factory default settings in step S15 will be given an option in step S16 to either exit from this decision making process or to return to the selection of user programs described above with respect to step S6-S15. A user who chooses not to exit this decision making process will be returned to step S6. An operator who chooses to exit will be returned to the primary process of FIG. 2 at input location H.

An operator who has chosen not to select user programs or who has completed the selection of user programs, as outlined above and shown in the preferred screen images of FIGS. 6-11, will be directed by the processor 14 to step S17 in FIG.

Figure 14:
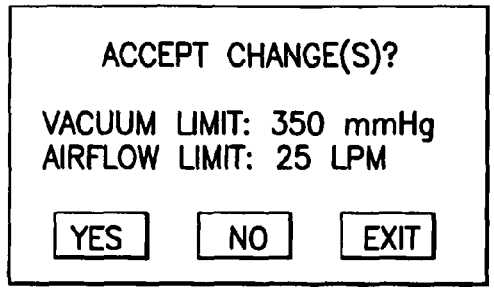
FIG. 14 is a schematic illustration of a eleventh preferred display provided by the LCD display of the apparatus.

2. In step S17, the processor 14 will display the current setting with a screen display similar to the preferred screen display of FIG. 12. The processor 14 then will give the operator the option in step S18 of choosing whether to accept the current settings. An operator who chooses to accept the current settings (step S19) will be directed to input J for commencing the operation of the aspirator 10. An operator who chooses in step S18 and in FIG. 12 not to accept the current settings will be directed to step S20 by the processor 14. The processor 14 also will cause the display 18 to display an image such as the preferred image of FIG. 13 as part of step S20. The operator then will use the rotary encoder push button switch 60 with the FIG. 13 display to make changes to the current settings. The processor 14 then will require the operator in step S21 to affirm the acceptance of the changed current settings. An operator could choose to exit (FIG. 14) this part of the decision making and will be returned to step S19 and then to input location J for starting the operation of the aspirator 10. An operator could choose in step S19 not to accept the changes (FIG. 14). Under these conditions, the processor 14 will direct the operator back to step S20 for further changing the current settings. However, the processor 14 further will give the operator the option in step S21 and FIG. 14 to accept the changes. The processor 14 then will direct the operator to step S22 and onto the start of operations as indicated at step S23. The operator also will be directed to step S23 (via input J) if the operator had chosen in step S4 to begin operations with the previous setting or if the operator had chosen in step S19 to begin or continue operations with the current settings.

Figure 16A:
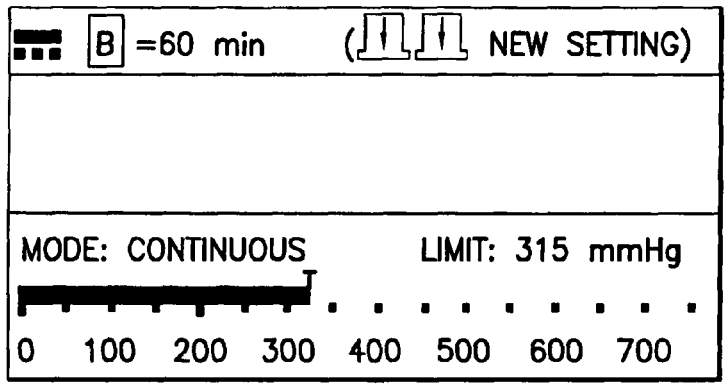
FIGS. 16A and 16B are schematic illustrations of a thirteenth preferred display provided by the LCD display of the apparatus.
Figure 16B:
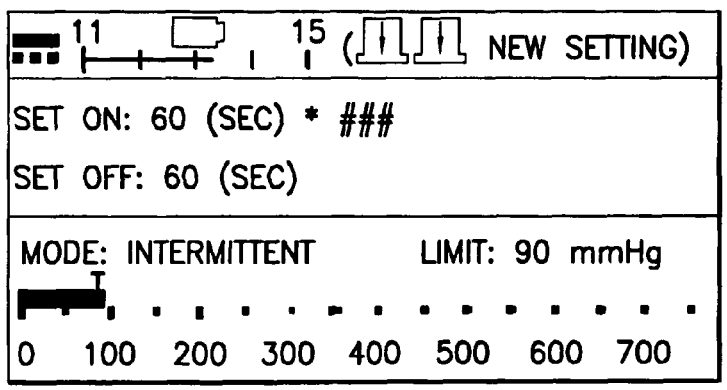

The processor 14 will cause the display 18 to display operating screens as shown, for example, in FIGS. 16A and 16B. The version of the operating screens shown in FIGS. 16A and 16B will be displayed and will vary in accordance with sensed operating conditions throughout the entire operation of the aspirator 10.

Figure 15:
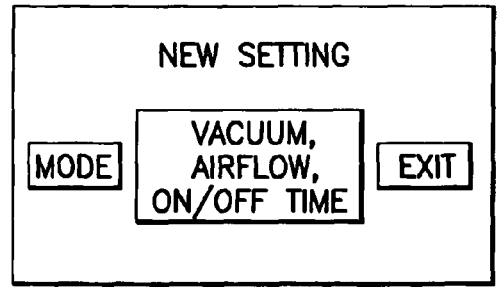
FIG. 15 is a schematic illustration of a twelfth preferred display provided by the LCD display of the apparatus.

The operation indicated generally by step S23 normally will continue for a considerable time and can be monitored on the display, as shown in FIGS. 16A and 16B. However, the operation may be interrupted intentionally by the operator or due to unintended operating conditions. This interruption of the operation at step S23 is assessed by the processor 14 at step S24. More particularly, an operator may determine that operational settings need to be changed. Under these conditions, the operator will press the rotary encoder push button switch 60 twice in succession. This double pressing of the switch 60 identified in step S24 will cause the processor to proceed to step S25 and to the preferred screen image shown in FIG. 15. The operator then uses the rotary encoder push button switch 60 of FIG. 1B to choose a new mode (step S26) vacuum, airflow, on/off time parameter (step S27) or exit (step S28). An operator who chooses in step S26 to select a new mode will be directed by the processor 14 to input location B and step S4. An operator who chooses to select a new setting of vacuum, airflow, on/off time in step S27 will be directed by the processor 14 to input location C and step S20 as described above. An operator who chooses in step S28 to exit will be directed by the processor to input location D and step S19 and further to input location J as described above for beginning the operation.

If the operation of step S23 is interrupted and if step S24 determines that the encoder 60 was not pressed twice, the processor 14 will determine whether the alarm 56 has been actuated. If the alarm 56 has not been actuated, the processor will return to step S23 to continue operation. If the processor 14 determines in step S29 that the alarm has been actuated, the processor 14 will proceed to input location K shown in FIG. 17. FIG. 17 shows the preferred logic employed by the processor 14 to determine the reason for the alarm. In step S30, the processor 14 will determine whether the battery is low or has failed. If the battery is low, the processor in step S31 will cause the display 18 to advise the operator that the alarm can be muted and to advise the operator as to conditions that should be undertaken to address the low battery condition. The processor 14 determines in step S32 whether the alarm 56 has been muted. If the alarm 56 has not been muted, the audible and visual alarm signals will remain active as indicated by step S33. If the alarm 56 has been muted as determined in step S32, then the display will include an icon in step S34 confirming that the alarm has been muted. A predetermined mute period is programmed in the processor 14. In step S35, the processor 14 will determine whether the mute period has ended. If the mute period is continuing, as determined in step S35, the processor 14 will ensure that the message of step S34 continues to be displayed. If the mute interval has elapsed, as determined in step S35, the processor 14 will return to step S30.

The processor 14 may determine in step S30 that the battery is not low. Under this condition, the processor will continue to step S36 for determining whether external power is low. If the processor 14 determines in step S36 that the external power is low, then the processor will proceed to steps S37-S41 which substantially parallel the steps S31-S35 as described above. If the processor 14 determines in step S36 that the external power is not low, then the processor will proceed to step S42 for determining whether the external power has failed or become disconnected. The processor 14 will proceed to step S43 if a determination has been made that the external power has failed or has become disconnected. More particularly, step S43 will give the operator the option of canceling the alarm message. The status of the alarm 56 is assessed in step S44. Here the processor will return to step D of FIG. 2 if the alarm has been canceled. Thus, the processor 14 will continue through the operation, as indicated at input location J and step S23. On the other hand, the external power fail/disconnect alarm message will continue at step S45 if the operator has not canceled the alarm 56 in step S44.

The portion of FIG. 17 from steps S30 through steps S45 assume that external power can be supplied or restored or a new battery can be activated so that the operation of step S23 can proceed. However, the alarm sensed in step S29 may be attributable to other causes. Hence, if the alarm 56 is sensed in step S29 and is not attributable to power related issues of steps S30, S36 and S42, the processor 14 will proceed to steps S46-S49 sequentially. In particular, step S46 determines whether a high vacuum condition exists. This may be determined by input received by the processor 14 from the closed loop control feedback signal and control lines 38 and 40 that connect the processor 14 to the valve 30 and the transducer 31. The determination in step S46 that a high vacuum exists will cause the processor 14 to transmit a signal to display 18 for displaying a high vacuum message. Additionally, audible and visual alarm signals remain active and cannot be muted. Furthermore, the processor 14 will cease operation of the aspirator 10. This problem can be cleared by recycling the on/off switch 52. However, further service may be required if the condition persists.

Step S47 determines whether the pump motor 32 has failed. This determination may be made by the connection 37 of the closed loop control signals in the control lines to and from the processor 14 and the motor speed control and tachometer 36. Once again, a sensed pump failure in step S47 will cause the operation to cease. Power can be recycled by operating the switch 52. However, service may be required if the pump failure persists, and in this circumstance, the display 18 will indicate the need for such service. As with the high vacuum condition sensed in step S46, the pump failure sensed by step S47 does not permit a muting of the alarm.

Step S48 determines whether the self check of step S2 in FIG. 2 has occurred. The determination in step S48 that the start-up self check has failed will cause operation to cease. The alarm 56 cannot be muted and operation is not allowed. Display 18 will display an appropriate service message.

Step S49 determines whether there is a system failure that is not addressed by any of steps S30, S36, S42, S46, S47 or S48. Operation will cease if a system failure is sensed. However, a determination in step S49 that there is no system failure will cause the processor to commence operation again at input location J and step S23.

The preceding paragraphs describe optional ways for changing settings using the processor 14. It should be understood, however, that the aspirator 10 continues to operate at its current setting until a change has been accepted. Furthermore, a change in a setting may be initiated but not completed for any number of reasons. Accordingly, the processor is programmed to return the screen to its previous setting image (e.g., FIGS. 16A, 16B) if there is a pause in the setting change greater than the pre-programmed amount of time.

While the invention has been described with respect to a preferred embodiment, it is apparent that various changes can be made without departing from the scope of the invention as defined by the appended claims. For example, the apparatus and process has been described with respect to user input from a rotary encoder push button switch 60. However, a touch screen input can be provided as well. Of course, the screen images illustrated herein are only preferred examples, and many other screen images can be developed to convey similar information and to trigger similar decision making processes. Additionally, the user input can be provided from a remote location and may include input provided from the keyboard of a computing device.

What is claimed is:

1. An aspirator comprising:
    a vacuum pump for producing a vacuum pressure;
    a motor for driving the vacuum pump;
    a manifold having a downstream side in communication with the vacuum pump and an upstream side for communicating with a patient;
    a valve communicating with the manifold and being operable for controlling vacuum characteristics across the manifold;
    a sensor in communication with the manifold for sensing actual vacuum pressure characteristics across the manifold;
    a barometer for sensing ambient atmospheric pressure; and
    a processor for controlling the motor and the valve for altering the actual vacuum pressure across the manifold and airflow through the manifold to achieve at least one operational characteristic specified by the processor, the processor being in two-way communication with the valve and the manifold for providing a closed-loop feedback with the valve and the manifold for altering the actual vacuum pressure across the manifold and the airflow through the manifold in response to sensed conditions, the processor further comprising an operational mode selecting switch for selecting one of a plurality of preset optional operational modes corresponding respectively to a plurality of optional medical uses, each operational mode defining a predetermined or determinable vacuum pressure and air flow rate, the processor further being connected to the barometer and further being operative for controlling at least one of the motor and the valve in view of ambient atmospheric pressures.

2. The aspirator of claim 1, further comprising an alarm connected to the processor and operative to generate audible and visual alarm signals in response to at least one of plural failure modes sensed by the processor, a mute switch being provided for permitting a muting of the audible alarm in response to at least one type of failure mode while being inoperative for muting the audible alarm in response to at least one other type of failure mode.

3. The aspirator of claim 2, further comprising at least one power source for powering the processor, the motor and the valve, the alarm being operative to produce an alarm signal in response to at least a partial power failure.

4. The aspirator of claim 3, wherein the power source comprises a battery and wherein the alarm produces an alarm signal in response to a failing battery.

5. The apparatus of claim 4, wherein the power source further comprises means for connection to a supply of AC or DC power, the alarm being operative to generate an alarm signal in response to at least one of a low external power level, an external power failure and an external power disconnect.

6. The aspirator of claim 2, wherein the processor is operative to compare actual vacuum pressure sensed by the sensor to a maximum allowable vacuum pressure level and to terminate operation of the aspirator in response to an actual vacuum pressure at least equal to the maximum allowable vacuum pressure the mute switch being inoperative for muting the alarm if the actual vacuum pressure is at least equal to the maximum allowable vacuum pressure.

7. The aspirator of claim 1, wherein the processor further includes at least one operator input switch for permitting an operator to select at least one of the specified operational characteristics.

8. A method for providing medical aspiration, said method comprising:
    providing an aspirator having a variable controllable vacuum pump for producing a vacuum pressure and an airflow, the aspirator further having a valve for controlling the vacuum;
    selecting one of a plurality of optional preset operational modes corresponding respectively to a plurality of optional medical uses, each of the operational modes defining a specified airflow rate and a specified vacuum pressure;
    measuring an actual airflow rate and an actual vacuum pressure across the valve;
    comparing the specified airflow rate to the actual airflow rate;
    comparing the specified vacuum pressure to the actual vacuum pressure;
    automatically adjusting the vacuum pump and the valve for conforming the specified and actual airflow rates and the specified and actual vacuum pressures; and
    measuring ambient atmospheric pressure and adjusting the vacuum pump to compensate for variations in ambient atmospheric pressure.

9. The method of claim 8, further comprising delivering power to the vacuum pump from a power source; measuring the power level from the power source; and adjusting at least one of the vacuum pump and the valve in response to a change in the power level.

10. The method of claim 9, further comprising generating an alarm signal in response to certain sensed conditions.

11. The method of claim 8, wherein the step of selecting one of a plurality of optional operational modes comprises selecting a user programming mode and inputting a user-determined vacuum pressure level and airflow rate.

\* \* \* \* \*